United States Patent [19]

Leying et al.

[11] Patent Number: 5,955,271
[45] Date of Patent: Sep. 21, 1999

[54] METHOD AND KITS FOR DETERMINING MESSENGER RNA MOLECULES IN A SAMPLE

[75] Inventors: Hermann Leying, Bichl; Matthias Hinzpeter, Munich; Hans-Peter Fritton, Mörlenbach; Heiko Wittor, Tutzing, all of Germany

[73] Assignee: Boehringer Mannheim GmbH, Germany

[21] Appl. No.: 08/681,015

[22] Filed: Jul. 22, 1996

[30] Foreign Application Priority Data

Jul. 21, 1995 [DE] Germany ............... 195 26 431

[51] Int. Cl.⁶ ............... C12P 19/34; C07H 19/00
[52] U.S. Cl. ............... 435/6; 435/91.1; 435/91.2; 435/91.51; 536/22.1
[58] Field of Search ............... 435/6, 810, 91.1, 435/91.2, 91.51; 536/22.1, 25.32, 25.4

[56] References Cited

U.S. PATENT DOCUMENTS

| | | | |
|---|---|---|---|
| 5,354,657 | 10/1994 | Holtke | 435/6 |
| 5,424,189 | 6/1995 | Oberst | 435/6 |

FOREIGN PATENT DOCUMENTS

| | | | |
|---|---|---|---|
| 0 344578 | 12/1989 | European Pat. Off. | G01N 33/531 |
| 90060452 | 6/1990 | WIPO . | |
| 90/11369 | 10/1990 | WIPO . | |
| 93/09250 | 5/1993 | WIPO . | |
| 9315228 | 8/1993 | WIPO | C12Q 1/68 |
| 9010716 | 9/1993 | WIPO | C12Q 1/68 |

OTHER PUBLICATIONS

Reyes–Engel, et al. "Direct Quantitation of specific mRNA using a selected biotinylated oligonucleotide by free solution capillary electrophoresis" Nucl. Acids Res. 21(s): 759–60 (1993).

Cuddy, et al., "RT–PCR with affinity captured mRNA" Nucl. Acids Res. 21(9): 2281(1993).

Derwent AN 94–337443 (corresponding to JP 06 261800) Sep. 20, 1994.

*Primary Examiner*—Kenneth R. Horlick
*Assistant Examiner*—Joyce Tung
*Attorney, Agent, or Firm*—Fulbright & Jaworski, LLP.

[57] ABSTRACT

The invention involves methods and kits useful in determining specific mRNA molecules. The methods can be carried in a single reaction vessel, in that both reverse transcriptase and amplification can be carried out in the same, heat stable reaction vessel.

26 Claims, 1 Drawing Sheet

METHOD AND KITS FOR DETERMINING MESSENGER RNA MOLECULES IN A SAMPLE

FIELD OF THE INVENTION

The invention involves a method, reagent and kit for the specific determination of RNA, such as poly(A) containing sequence (mRNA), using coated solid phases. The methods of the invention can be used to quantify and detect RNA, mRNA in particular, from mixtures of total RNA and extracts of cell cultures and tissue cells. The method does not require preceding enrichment or isolation of the RNA.

BACKGROUND AND PRIOR ART

Almost all mRNA present in eukaryotic cells terminates in a sequence of approximately 20 to 250 adenosine nucleotides, a fact that is used in most mRNA purification methods. Today, a standard method for the detection and quantification of mRNA is the combined use of reverse transcriptase (RT) and PCR (RT-PCR) (Larrick, J. W., Trends Biotechnol. 10, 146–152 (1992); Kawasaki, E. S., PCR Protocols: A Guide to Methods and Applications (eds. Innis, M. A. et al.), Academic Press, San Diego, Calif. (1990)). The initial material for this method is purified total RNA (rRNA, tRNA, mRNA) or purified mRNA. The latter is used because the enzymes, particularly polymerases, used in the RT-PCR are easily inhibited by contamination.

The purification of RNA and mRNA is known from several methods including extraction with organic solvents (e.g. phenol/chloroform), purification via oligo(dT)-cellulose, or isolation with the aid of oligo(dT)-coated magnetic particles (Sambrook, J., Fritsch, E. F. and T. Maniatis, Molecular Cloning: A Laboratory Manual, Cold Spring Harbor Laboratory Press, Cold Spring Harbor, N.Y., 2nd edition (1989); Farrell, R. E., RNA Modologies: A Laboratory Guide for isolation and Characterization, Academic Press (1993)). These methods are complex and difficult to automate.

Purification of mRNA can also be achieved via hybridization of the poly(A)-carrying 3'-end of the eukaryotic mRNA, using biotinylated oligo(dT). Hybrids of biotin-oligo(dT) and mRNA are then bound to avidin or streptavidin-coated magnetic particles and isolated. This method has a drawback in that only large amounts of mRNA hybrid can be isolated; the mixture is, hence, not sensitive enough for the detection of specific mRNAs.

An assay using RT-PCR on solid phase, such as magnetic particles, was then developed to address this problem. A drawback of this method is, however, that after binding and washing of the mRNA, the magnetic particles must be transferred into reaction vessels that are suitable for PCR. These vessels must be especially stable to heat, in view of the elevated temperatures at which PCR is carried out. This requires another separation step. Each added step in a reaction compromises it further.

SUMMARY OF THE INVENTION

It is, hence, an object of the invention to provide an improved method for the determination of mRNA which eliminates the drawbacks known from prior art.

This object is accomplished by a method for the specific determination of mRNA, characterized in that a lysis and/or hybridization buffer is added to a suitable sample material and, if necessary, homogenized, the sample solution is brought into contact with a hybridization partner which is complementary to at least one sequence in the sample, an aliquot of the mixture is transferred into a heat-stable, RNase-free reaction vessel coated with an organic chemical compound where it is incubated for at least 10 seconds in a temperature range of approximately 4 to 50° C., the supernatant is removed from the reaction vessel and the reaction vessel may be washed, one or more times with a suitable buffer solution, a mixture which contains an enzyme with reverse transcriptase (RT) activity, or an enzyme with RT- and heat-stable DNA-polymerase activity is then added and incubated at approximately 30 to 75° C., over a time sufficient for the relevant enzymatic reaction to take place, if necessary, the mixture is removed and washed with washing buffer, if necessary, another mixture containing at least one heat-stable DNA polymerase and two specific DNA primers is added into the reaction vessel and incubated under conditions favoring amplification, and if necessary, the DNA contained in the mixture is separated, particular by means of electrophoretical procedures, and then detected.

DETAILED DESCRIPTION OF PREFERRED EMBODIMENTS

Figure 1:
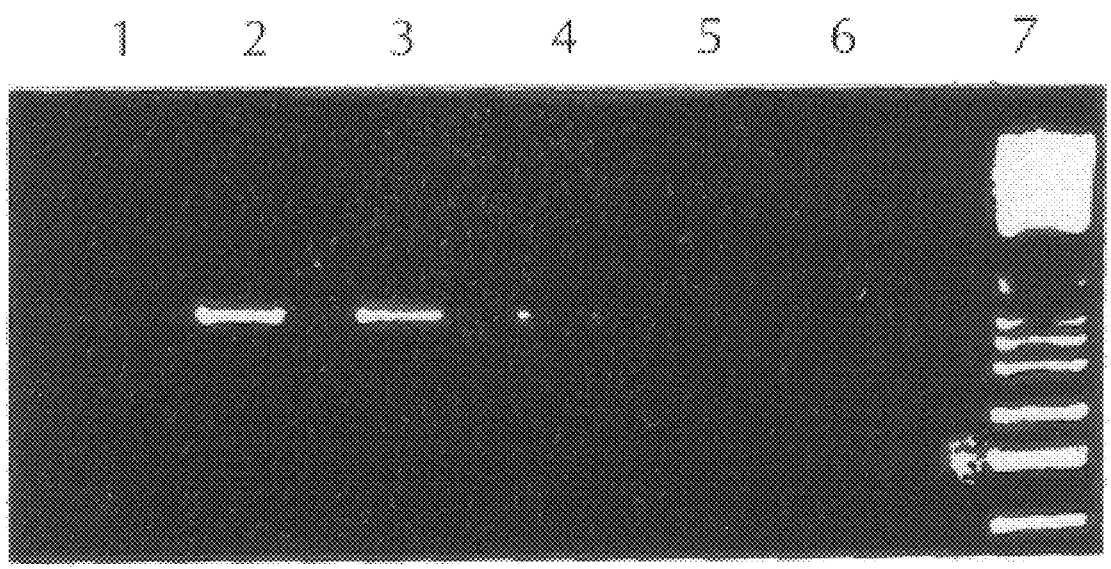
FIG. 1 presents results obtained using this invention to determine G3PDH specific mRNA. Lane 1 is a control, using cells but no reverse transcriptase. Lanes 2–5 show results from a dilution series using cell lysates. In lane 2, 7500 cells were lysed. Lane 3 corresponds to 750, lane 4 shows 75 cells, and in lane 5, 7.5 cells. Lane 4 shows only one visible lane. In lane 6, a control is presented, wherein 1×RT mix was used, without cells. Lane 7 is a DNA molecule weight standard, used because the molecular weight of G3PDH mRNA is well known.

The invention is particularly advantageous because isolation and purification of mRNA from the corresponding sample materials are carried out in a vessel used for the reverse transcriptase (RT) reaction and PCR as well. Sample preparation (isolation and purification), transcription, and/or amplification (RT-PCR) are carried out in one single reaction vessel.

In addition to pure mRNA fractions, the sample material to be analyzed may include natural and artificial mixtures of total RNA (rRNA, tRNA, mRNA), as well as fractions (e.g., cell lysates) obtained from cell cultures and tissue cell extracts, and/or tissue homogenates of human or animal origin, and plant extracts.

Suitable lysis and/or hybridization buffers are based on buffering substances which exhibit good buffering capacity at a pH value between approximately 5–10, preferably between pH 7.0 and 8.5. Corresponding buffering substances are, for example, Tris.HCl, HEPES, MOPS, or Tris.borate.

Buffers which are suitable for the method of the invention can contain a disulfide-reducing reagent, such as dithioerythritol, dithiothreitol, or mercaptoethanol, preferably at a concentration between 0.01 and 1% (w/v). It has proven to be advantageous to add a denaturing substance such as a detergent at a relatively high concentration to the buffering systems. Dodecylsulfate salts or the corresponding derivatives, at a concentration of 0.1 to 15% (w/v) have proven to be particularly advantageous; guanidinium thiocyanate salts and its derivatives, at a concentration range between approximately 1 to 7M, particularly between 1 and 5M are particularly useful when dealing with RNase-rich tissue. Experience has shown that it is particularly advantageous when the solution used for the determination is almost free of RNase activities. This means the maximum residual activity of RNase must not exceed 5%.

The buffering systems used in the invention can also contain salts, such as lithium chloride, or other additives. It has proven to be particularly advantageous when an additional RNase inhibitor such as one obtained from placenta is present, and/or the buffering solution is sterilized and/or decontaminated with dimethyldicarbonate or diethylpyrocarbonate prior to use.

"Hybridization partner" as used herein refers to the well known property of nucleic acid molecules to hybridize as pairs, using well known principles of base complementarity. Exemplary of hybridization partners are poly- and oligonucleotides, oligo-dT molecules, oligo-dU molecules, primers, specific probes, nucleotide derivatives, including molecules which include nucleotides but do not consist of them (e.g., pNAs) and so forth, any and all of which hybridize to mRNA generally, or to specific mRNA molecules. The specific hybridization partner used can be determined by the skilled artisan, based upon the particular method being carried out. Preferably, the hybridization partner is 15–30 nucleotides in length. More preferably, it is about 20 nucleotides in length; however, the partner's length may also vary, within established protocols for hybridization.

The label hybridization partner may include haptens, protein with antigen and/or antibody structure, and so forth. Biotin bound to an oligo(dT) sequence has proven to be particularly suitable as it can be linked to a solid phase via streptavidin or avidin; this requires that the organic chemical "coating substance" referred to supra and infra be avidin or streptavidin. Alternatively, the coating substance can also be oligo(dT) nucleotides or suitable chelate compounds which are suitable for fixing corresponding probes via hybridization or complex formation. Immobilization of mRNA to avidin or streptavidin-coated solid phases and/or reaction vessels is a very familiar and reliable method for mRNA extraction for subsequent transcription or amplification.

It is also possible to use other labels to fix mRNA to the solid phase. These labels are not set forth here, as they are well known to the art. Nucleotide probes such as, oligo(dT) probes, can be obtained according to known methods or be purchased from commercial suppliers.

In practice, polyadenylated mRNA-containing sample material is combined with an aqueous solution which contains a labeled oligo(dT) probe. Hybridization is carried out, preferably at approximately 37° C. and is usually completed after only a few seconds. A period of 10 seconds to 10 minutes, preferably 5 minutes has in most cases proven to be sufficient for hybridization.

An aliquot of the biotin-oligo(dT)-mRNA hybrid containing solution is then directly added to the coated, heat-stable reaction vessel. Under optimal conditions, the volume of the aliquot is approximately that of the respective vessel volume and should not contain more than approximately 5 pmol of the hybrid. A sample of approximately 20 to 200 µl lysate is usually sufficient. For immobilization on the coated solid phase, only a few seconds of incubation time, i.e. about 10 seconds and a temperature of approximately 4 to 50° C., preferably about 37° C., are usually sufficient; to be on the safe side, the process is usually continued for 1 to 10 minutes.

Subsequently, the rest of the lysate is removed and the bound RNA is thoroughly washed (approx. 5 times) and the washing buffer is then quantitatively removed such that a reverse transcriptase (RT) reaction can be carried out. In addition to conventional buffer substances and salts, a typical mixture of the RT reaction also contains magnesium ions, all four deoxy-nucleotide triphosphates (dNTPs), an enzyme with RT activity, preferably an enzyme with both RT and heat-stable DNA-polymerase activity, such as DNA polymerase from *Thermus thermophilis* (Tth), and, preferably, an RNase inhibitor. An aliquot of such a mixture (approximately 20 to 200 µl) is then added to the reaction vessel. AMV- or M-MuLV-RT, the latter particularly in its RNase H$^-$ form as described by U.S. Pat. No. 5,244,797, are particularly preferred as the enzymes with RT activity. There are preferably used at a concentration of between 0.01 to 5 U/µl. The preferred final RT concentration is between 0.1 and 1.0 U/µl. Experience has shown that RTs of other virus types and sources can also be used in accordance with the invention.

Incubation for the cDNA synthesis can be carried out at appr. 30 to 75° C., preferably between 35 and 45° C. and usually takes 30 to 120 minutes. In many cases, an incubation temperature of approximately 42° C. has proven to be particularly advantageous.

After completion of the reaction, the reaction solution is removed and the bound remainder is again washed thoroughly with washing buffer. Subsequently, a defined volume of PCR mix is added to the coated reaction vessel, usually 20–200 µl, and incubated under less stringent conditions than those employed previously. An optimum PCR mix contains a suitable buffer system, e.g., the buffer components given in Maniatis et al. (2nd ed. 1989, pages 14.15 to 14.17), magnesium ions in a concentration range of approximately 0.5 to 5.0 mM, a defined amount of heat-stable DNA polymerase, preferably between 5 to 300 mU/µl, all four dNTPs, each at a concentration of 0.05 to 0.5 mM, preferably each approximately 0.2 mM and at least two DNA primers between 0.1 and 1.0 pmol.µl, preferably each at approximately 0.4 pmol/µl.

The PCR reaction itself is carried out according to parameters known to the expert, such as a first cycle at 95° C. (5 minutes), 50° C. (2 minutes) and 72° C. (3 minutes). Subsequent cycles (a total of approximately 40 cycles) can then be carried out according to the following scheme: 95° C. (1 minute), 50°0C. (2 minutes) and 72° C. (3 minutes and, in the last run, 20 minutes). Other parameters may also be used.

After completion of the PCR reaction, the solution containing the transcribed and amplified DNA is removed from the reaction vessel and separated, e.g., electrophoretically, and detected with, e.g., ethidium bromide.

Another advantageous embodiment of the invention is that the RT and PCR reactions are not carried out sequentially, but in a coupled reaction without an intermediate washing step. in such a simultaneous process, the RT solution must not be removed after completion of the RT reaction. In a particularly advantageous embodiment, a bifunctional enzyme is used which exhibits both RT and DNA polymerase activity and is heat-stable. In such a 1 vessel/1 buffer embodiment, an incubation time of approximately 5 minutes, up to 1 hour, has proven to be particularly advantageous.

Conditions for an RT and/or PCR reaction described in Maniatis et al., Molecular Cloning: A Laboratory Manual, Cold Spring Harbor Laboratory Press, Cold Spring Harbor, N.Y., 2nd edition (1989) have proven to be particularly suitable.

The DNA mixture obtained in accordance with the invention is usually detected following electrophoretic separation and using suitable hybridization methods (Southern Blot, ELISA). It is, however, also possible to directly detect the DNA mixture without prior separation. The expert is familiar with such methods and these are not repeated here. It was thus possible to detect mRNA which corresponds to protein activity below the activity expect of a single cell.

The preparation of coated solid phases and/or reaction vessels is known to the expert as in e.g., EP 0331127, incorporated here by reference. When streptavidin and/or avidin-coated carrier materials are used, the reaction vessels disclosed in EP 0344578 incorporated by reference have proven to be particularly advantageous.

Another aspect of the invention is a reagent and/or a kit for the determination of mRNA which includes the following components:

(a) lysis and hybridization buffer, (b) buffer solution with a labeled nucleotide probe that carries a poly(A) complementary sequence, (c) washing buffer, (d) a mixture containing an enzyme with reverse transcriptase activity, (e) a mixture containing at least one heat-stable DNA polymerase, and (f) a device having at least one coated, RNase-free reaction vessel.

The method of the invention has proven to be particularly preferred with a biotin-labeled oligo(dT) probe is used and when the solid phase suitable for the immobilization of the hybrid is coated with streptavidin and/or avidin. Moreover, a preferred kit is one which contains one mixture (d') instead of two mixtures (d) and (e); said mixture (d') includes an enzyme with both RT and heat-stable DNA-polymerase activity, the features that are disclosed in connection with the method of the invention also apply to kit.

The following examples illustrate the invention in greater details.

EXAMPLE 1

A streptavidin-coated PCR vessel was used to carry out RT-PCR directly from cells without prior isolation of the RNA.

Cells were lysed in lysis and/or hybridization buffer, the DNA was separated, the mRNA immobilized by hybridizing the poly A$^+$ tail with BidT$_{20}$ (biotinylated oligo dT, containing 20 T residues) and binding it to the streptavidin matrix in the reaction vessel. Synthesis of the corresponding cDNA was then achieved with the aid of a reverse transcriptase; using specific primers, the amplification of the specific transcript was achieved via PCR followed by quantification, e.g., in agarose gel via ethidium bromide staining.

This examples describes an RT-PCR carried directly from human K562 cells for the detection of mRNA of G3PDH.

All components used are manufactured by Boehringer Mannheim GmbH, except the PCR primers for human G3PDH-mRNA (983 bp), which were obtained from Clontech. The buffer (lysis/hybridization buffer) and the RT and PCR mixtures were prepared as follows:

1) Lysis/hybridization Buffer
   a) Detergent buffer (volume for 250 ml):
      25.0 ml Tris.HCl, 1M, pH 7.5 (4° C.)
      15.0 ml LiCl, 5M
      5.0 ml EDTA, 0.5M, pH 8.0
      25.0 ml lithium-dodecylsufate
      193.0 ml 1,4-diethioerythritol
      180.0 ml redist. water
      (The autoclaved stock solutions are stable at RT).
   (b) GTC buffer
      4.0 ml guanidinium thiocyanate (GTC)
      0.1M Tris-HCl, pH 8.0
      1.0% 1,4-dithiothreitol (w/v)
      0.5% laurosylsarcosine (w/v)
      (store at −20° C.)
2) Biotin-labeled Oligo(dT) Probe (volume for 20 μl)
   19.0 μl redist. water
   1.0 μl biotin-oligo(dT)$_{20}$sample (100 pmol)
3) Washing Solution (volume for 250 ml)
   2.5 ml Tris.HCl, 1M, pH 78.5 (4° C.)
   10.0 ml LiCl, 5M
   0.5 ml EDTA, 0.5M pH 8.0
   237.0 ml redist. water
4) RT Mix (volume for 1 ml)
   204.1 μl Tris-HCl, 10 mM, pH 7.4
   51.0 μl Tris-HCl, 1M, pH 8.3 (42° C.)
   142.0 μl KCl, 1M
   40.8 μl MgCl$_2$, 250 mM
   102.0 μl dNTPs, 10 mM each
   40.8 μl 1,4-dithioerythritol, 100 mM
   20.0 μl RNase inhibitor (40 U/μl)
   398.4 μl redist. water
   32.0 μl AMV reverse transcriptase (25 U/μl)
5) PCR Mix volume for 1 ml)
   100.0 μl Taq buffer (10 times)
   20.0 μl dNTPs, mM each
   4.0 μl primer, 100 pmol/μl each
   867.0 μl redist. water
   5.0 μl taq polymerase (5 U/μl)

All solutions and/or the redistilled water used for their preparation should be treated with dimethyldicarbonate (DMDC) or diethylpyrocarbonate (DEPC) to eliminate any RNases which might be present.

Cell lysis and immobilization of the mRNA in the streptavidin coated reaction vessel.

K562 cells exhibited a logarithmic growth curve with 3×10$^5$ cells/ml. A 1 ml cell suspension was removed by centrifugation at 300 g for 5 minutes and washed once with ice-cold PBS. The pellet was stored in liquid nitrogen. The frozen pellet was then resuspended in 200 μl lysis buffer, the DNA was sheared by passing it through a 0.8 ml syringe (6 times); a log dilution series was prepared from the lysate by pipetting portions of 20 μl into the prepared lysis buffer (180 μl). Portions of 5 pmol BidT$_{20}$ were pipetted into the mixture and hybridized for 5 minutes at 37° C. Portions of 50 μl of the mixtures were pipetted into streptavidin-coated PCR vessels and incubated for 3 minutes at 37° C. to bind hybrids thereto. Subsequently, the solution was removed by means of pipetting, and the vessels were washed on ice 4 times with 250 μl of washing buffer each time.

cDNA synthesis

Portions of 50 μl 1× RT mix were pipetted into the individual vessel segments and incubated for approximately 2 hours at 42° C. As a control, the highest RNA concentration with RT mix without the reverse transcriptase was used, as was a simple containing no RNA with RT mix with RT as another control in another segment. Subsequently, the RT was thermally denatured for 10 minutes at 65° C. and washed 4 times with 250 μl of washing buffer each time.

Amplification via PCR

Portions of 50 μl of 1× PCR mix were pipetted into the individual vessel segments and the PCR runs were carried out in a thermocycler according to the manufacturer's instructions. After separation of the PCR products on a 2% agarose gel (with ethidium bromide) at 100 V for 35 minutes an amplification product derived from human G3PDH-mRNA was detected.

EXAMPLE 2

The parameters of example 1 were used to determined β-actin-mRNA cell. Specific primers uswed were:

5'-CCAAGGCCAA CCGCGAGAAG ATGAC(SEQ ID NO: 1) (sense)

and

5'-AGGGTACATG GTGGTGCCGC CAGAC(SEQ ID NO: 2) (antisense)

The assay resulted in determination of β-actin mRNA corresponding to a protein activity below that expected for a single cell.

said reaction vessel having an interior coated with a chemical compound which binds to label on said labelled, hybridization partner, (e) incubating said aliquot at a temperature of from about 4° C. to about 50° C. for at least 10 seconds, (f) removing reaction solution from said reaction vessel, (g) washing any hybrids bound on the coated interior of said reaction vessel with a washing buffer, (h) adding a solution which contains an enzyme having reverse transcriptase activity, (i) incubating said solution at a temperature of from about 30° C. to about 75° C. for a time sufficient for said enzyme to reverse transcribe any mRNA contained in said reaction vessel, (j) removing said solution following incubation, (k) washing the interior of said reaction vessel with a washing buffer, (l) adding to said reaction vessel a solution containing at least one heat stable DNA polymerase, at least two primer molecules which hybridize to any reverse transcribed product formed in (h), and samples of all four

---

---

We claim:

1. Method for determining a specific mRNA molecule in a sample, comprising:

(a) adding at least one buffer to said sample, (b) contacting said sample with a labelled hybridization partner which is complementary to said mRNA molecule, (c) incubating said sample to form hybrids of said mRNA molecule and said hybridization partner, (d) transferring an aliquot of sample containing said hybrids to a heat stable, RNase free reaction vessel, nucleotides, under conditions favoring synthesis and amplification of DNA, and (m) determining DNA synthesized and amplified in (l) as a determination of said specific mRNA molecule present in solution phase.

2. Method for determining a specific mRNA molecule in a sample, comprising:

(a) adding at least one buffer to said sample, (b) contacting said sample with a labelled hybridization partner which is complementary to said mRNA molecule, (c) incubating said sample to form hybrids of said mRNA molecule and said labelled hybridization partner, (d) transferring an aliquot of sample containing said hybrids to a heat stable, RNase free reaction vessel, said reaction vessel having an interior coated with a chemical compound which binds to label on said labelled, hybridization partner, (e) incubating said aliquot at a temperature of from about 4° C. to about 50° C. for at least 10 seconds, (f) removing reaction solution from said reaction vessel, (g) washing any hybrids bound to the interior of said reaction vessel with a washing buffer, (h) adding a solution to said reaction vessel which contains an enzyme having both reverse transcriptase and DNA polymerase activity, at least two primer molecules which specifically hybridize to any reverse transcribed product, and samples of all four nucleotides, (i) incubating said solution under conditions favoring said enzyme reverse transcribing any mRNA followed by incubating said solution under conditions favoring synthesis and amplification of any reverse transcription product, (j) removing said solution, and (k) determining reverse transcription product synthesized in (i) as a determination of said specific mRNA molecule present in solution phase.

3. The method of claim 1 or 2, wherein said sample is a cell containing sample, wherein said buffer is lysis buffer.

4. The method of claim 3, further comprising homogenizing said sample prior to contact with said labelled hybridization partner.

5. The method of claim 1 or 2, wherein said sample is a cell free sample, wherein said buffer is a hybridization buffer.

6. The method of claim 3, wherein said cell containing sample comprises cultivated cells, animal tissue cells, human tissue cells, or plant cells.

7. The method of claim 5, wherein said sample is a total RNA containing cell extract.

8. The method of claim 3, wherein said lysis buffer contains a disulphide group reducing substance, a buffering agent at a pH of from 7.0 to 8.5, and a denaturing agent.

9. The method of claim 8, wherein said denaturing agent is a detergent.

10. The method of claim 8, wherein said lysis buffer further comprises an RNase inhibitor.

11. The method of claim 8, wherein said lysis buffer contains from 0.5% to 15.0% (w/v) of a dodecylsulfate salt, or guanidium thiocyanate at a concentration of 1M to 7M.

12. The method of claim 1 or 2, wherein said reaction vessel is coated with avidin of streptavidin, and said labelled hybridization partner is labelled with biotin.

13. The method of claim 1 or 2, wherein said hybridization partner is an oligo dT containing molecule, an oligo dU containing molecule, or a PNA derivative.

14. The method of claim 1 or 2, wherein said hybridization partner consists of from 15 to 30 nucleotides, said hybridization being carried out at 37° C., for a period of from 1 to 10 minutes.

15. The method of claim 1, wherein said enzyme having reverse transcriptase activity is AMV or m-MuLV reverse transcriptase, said solution having reverse transcriptase activity further comprising a sulfhydryl group containing agent, an RNase inhibitor, potassium ions, magnesium ions, and a buffering agent.

16. The method of claim 1 or 2, comprising incubating said enzyme having reverse transcriptase activity at a temperature of from 35° C. to 45° C.

17. The method of claim 1 or 2, wherein said enzyme having DNA polymerase activity is heat stable, said enzyme being added at 5 to 300 mU/μl, said primers being added at a concentration of about 0.1 to about 1.0 pmol/l, approximately 0.05 to about 0.5 mM of each nucleotide, and a buffering agent.

18. The method of claim 17, further comprising adding a magnesium ion.

19. The method of claim 2, wherein said enzyme having reverse transcriptase and DNA polymerase activity is heat stable, said method comprising incubating said enzyme for from about 5 minutes to about 1 hour.

20. Test kit useful for determining an mRNA molecule, comprising (i) a separate sample of each of
(a) a solution containing a labelled hybridization partner which binds to said mRNA molecule,
(b) a washing buffer,
(c) a solution containing an enzyme having reverse transcriptase activity, and (ii) a heat stable reaction vessel having an interior coated with a chemical compound which binds to label on said labelled hybridization partner.

21. The test kit of claim 20, further comprising a cell lysis buffer or a hybridization buffer.

22. The test kit of claim 21, further comprising a separation sample of an enzyme having DNA polymerase activity.

23. The test kit of claim 21, wherein said labelled hybridization partner is labelled with biotin, and said reaction vessel is coated with avidin or streptavidin.

24. Method for determining a specific mRNA molecule in a sample, comprising:

(a) combining said sample with at least one buffer and a labelled hybridization partner which is complementary to said mRNA molecule in a heat stable, RNase free reaction vessel which has an interior coated with a chemical compound which binds to label on said labelled hybridization partner, and incubating to form hybrids of said mRNA molecule and said hybridization partner, for at least 10 seconds at a temperature of from 4° C. to about 50° C.;

(b) removing supernatant from said reaction vessel;

(c) washing any hybrids bound on the coated interior of said reaction vessel with a washing buffer;

(d) adding a solution which contains an enzyme having reverse transcriptase activity;

(e) incubating said solution at a temperature of from about 30° C. to about 75° C. for a time sufficient for said enzyme to reverse transcribe any mRNA contained in said reaction vessel;

(f) removing said solution following incubation;

(g) washing the interior of said reaction vessel with a washing buffer;

(h) adding to said reaction vessel a solution containing at least one heat stable DNA polymerase, at least two primer molecules which hybridize to any reverse transcribed product formed in (g), and samples of all four nucleotides, under conditions favoring synthesis and amplification of DNA; and (i) determining DNA synthesized and amplified in (h) as a determination of said specific mRNA molecule present in solution phase.

25. Method for determining a specific mRNA molecule in a sample, comprising:

(a) combining said sample with at least one buffer, and a labelled hybridization partner which is complementary to said mRNA molecule in a heat stable, RNase free reaction vessel which has an interior coated with a chemical compound which binds to label on said labelled hybridization partner, and incubating to form hybrids of said mRNA molecule and said hybridization partner, for at least 10 seconds at a temperature of from 4° C. to about 50° C.;

(b) removing supernatant from said reaction vessel;

(c) washing any hybrids bound to the interior of said reaction vessel with a washing buffer;

(d) adding a solution to said reaction vessel which contains an enzyme having both reverse transcriptase and DNA polymerase activity, at least two primer molecules which specifically hybridize to any reverse transcribed product, and samples of all four nucleotides;

(e) incubating said solution under conditions favoring said enzyme reverse transcribing any mRNA followed by incubating said solution under conditions favoring synthesis and amplification of any reverse transcription product, (f) removing said solution, and (g) determining DNA formed in (e) as a determination of said specific mRNA molecule present in solution phase.

26. The method of claim 1, 2, 24, or 25, wherein said sample is impure RNA.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 25 nucleotides
      (B) TYPE: nucleic acid
      (C) STRANDEDNESS: single
      (D) TOPOLOGY: linear (ii) MOLECULE TYPE:  DNA (xi) SEQUENCE DESCRIPTION: SEQ ID NO: 1:

CCAAGGCCAA CCGCGAGAAG ATGAC                     25

(2) INFORMATION FOR SEQ ID NO: 2:

(i) SEQUENCE CHARACTERISTICS:
      (A) LENGTH: 25 nucleotides
      (B) TYPE: nucleic acid
      (C) STRANDEDNESS: single
      (D) TOPOLOGY: linear (ii) MOLECULE TYPE:  DNA (xi) SEQUENCE DESCRIPTION: SEQ ID NO: 2:

AGGGTACATG GTGGTGCCGC CAGAC                     25